United States Patent
Gruener

(10) Patent No.: US 8,082,791 B2
(45) Date of Patent: Dec. 27, 2011

(54) METHOD AND DEVICE FOR DETERMINING THE SOFTNESS OF SANITARY PAPERS AND TEXTILES

(75) Inventor: Giselher Gruener, Leipzig (DE)

(73) Assignee: Alexander Gruener, Leipzig (DE)

( * ) Notice: Subject to any disclaimer, the term of this patent is extended or adjusted under 35 U.S.C. 154(b) by 640 days.

(21) Appl. No.: 12/279,688

(22) PCT Filed: Jan. 23, 2007

(86) PCT No.: PCT/EP2007/050628
§ 371 (c)(1),
(2), (4) Date: Oct. 21, 2008

(87) PCT Pub. No.: WO2007/093484
PCT Pub. Date: Aug. 23, 2007

(65) Prior Publication Data
US 2009/0100916 A1    Apr. 23, 2009

Related U.S. Application Data

(60) Provisional application No. 60/823,099, filed on Aug. 22, 2006.

(30) Foreign Application Priority Data

Feb. 15, 2006   (DE) .................. 10 2006 007 678

(51) Int. Cl.
*G01N 3/14* (2006.01)
*G01N 3/40* (2006.01)
(52) U.S. Cl. ................. 73/573; 73/73; 73/159
(58) Field of Classification Search ............. 73/573, 73/73, 159, 581, 587, 597
See application file for complete search history.

(56) References Cited

U.S. PATENT DOCUMENTS

| | | | |
|---|---|---|---|
| 3,026,726 A | 3/1962 | Reading | |
| 3,060,719 A | 10/1962 | Pearlman | |
| 3,151,483 A | 10/1964 | Plummer | |
| 3,683,681 A | 8/1972 | Taylor | |
| 4,548,081 A * | 10/1985 | Wolthausen | 73/584 |

(Continued)

FOREIGN PATENT DOCUMENTS

DE    2835038 A1    2/1980
(Continued)

OTHER PUBLICATIONS

Robert S. Ampulski, "Methods for the Measurement of the Mechanicl Properties of Tissue Paper", International Paper Physics Conference, 1991, pp. 19-30.

C.M. Carr, "Technology Transfer—A Quality Control Tool From the Textile Industry", Paper Technology, Nov. 1993, pp. 27-28.

(Continued)

*Primary Examiner* — Jacques M Saint Surin
(74) *Attorney, Agent, or Firm* — Norris McLaughlin & Marcus, P.A.

(57) ABSTRACT

The invention relates to an apparatus and a method for determining the softness of a hygienic paper or textile with at least one ply, wherein an element (106) is arranged relative to a positionally fixed sample (P), with at least one ply, of the hygienic paper or textile such that it can move and is designed such that it can be adjusted with respect to the sample (P) with a penetration force (F) acting on the sample (P) being specified, wherein in the region of the oscillations being produced between sample (P) and the element (106), an oscillation sensor (116) is arranged which registers the noises produced during the relative movement of the element (106) acting on the sample (P).

25 Claims, 1 Drawing Sheet

U.S. PATENT DOCUMENTS

| | | | | |
|---|---|---|---|---|
| 4,735,087 A | * | 4/1988 | Hourani et al. | 73/597 |
| 4,869,101 A | * | 9/1989 | Dvorsky | 73/159 |
| 5,014,547 A | * | 5/1991 | Holroyd | 73/105 |
| 6,026,681 A | * | 2/2000 | Wunderer et al. | 73/159 |
| 6,486,962 B1 | * | 11/2002 | Telschow et al. | 356/503 |
| 7,191,657 B2 | * | 3/2007 | Maier et al. | 73/587 |
| 7,578,200 B2 | * | 8/2009 | Leveugle et al. | 73/801 |

FOREIGN PATENT DOCUMENTS

| | | |
|---|---|---|
| DE | 3020348 A1 | 12/1981 |
| DE | 19521427 A1 | 1/1997 |
| DE | 19543674 A1 | 5/1997 |
| DE | 19720864 A1 | 11/1998 |
| DE | 19812026 A1 | 9/1999 |
| EP | 1290405 A0 | 12/2001 |

OTHER PUBLICATIONS

Holger Hollmark, "Evaluation of Tissue Paper Softness", Tappi Journal, Feb. 1983, pp. 97-99.
English Language Abstract for DE 2835038, Feb. 21, 1980.
English Language Abstract for DE 3020348, Mar. 12, 1981.
English Language Abstract for DE 19720864, Nov. 12, 1998.
English Language Abstract for DE 19812026, Sep. 23, 1999.
English Language Abstract for EP 1290405, Dec. 13, 2001.
Hollmark Holger et al: "Measurement of tissue paper softness: A literature review" Nord Pulp Pap Res J; Nordic Pulp and Paper Research Journal 2004, vol. 19, Issue 3, pp. 345353, 2004.
English Language Abstract for DE 195 21 427, Jan. 2, 1997.
English Language Abstract for DE 195 43 674, May 28, 1997.

* cited by examiner

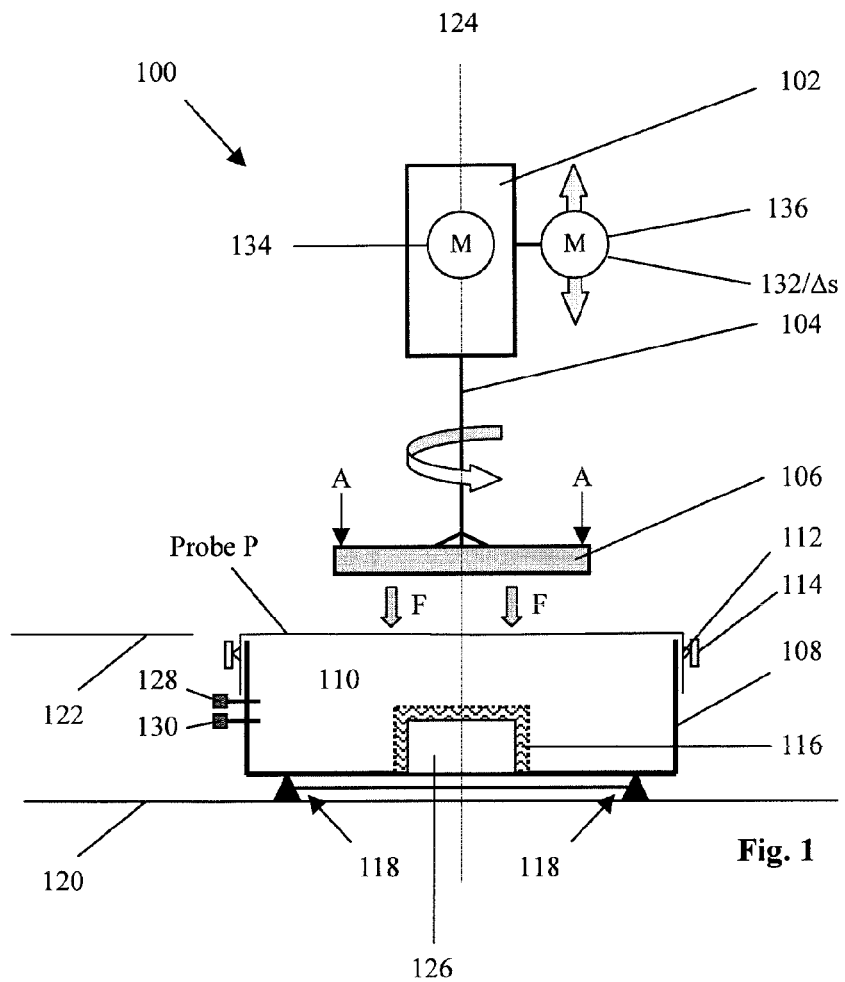
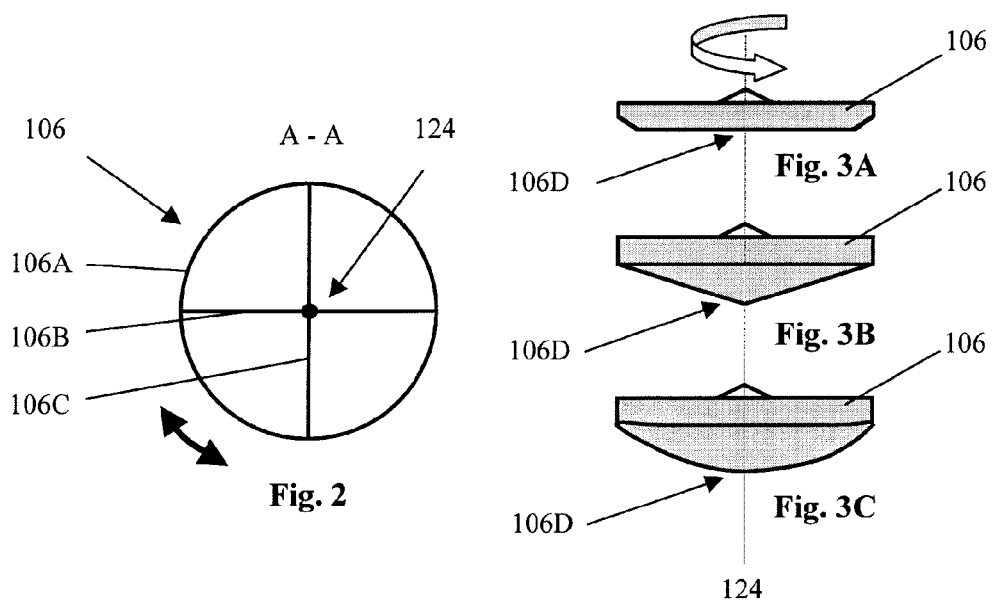

METHOD AND DEVICE FOR DETERMINING THE SOFTNESS OF SANITARY PAPERS AND TEXTILES

This application is a 371 application of PCT/EP2007/050628 filed Jan. 23, 2007, which claims priority to the German application DE 10 2006 007 678.8 filed Feb. 15, 2006 and United States application 60/823,099 filed Aug. 22, 2006.

The invention is directed to a method and a device for determining the softness of sanitary papers and textiles.

The name sanitary paper includes cellulose wadding, tissue and crepe paper and is manufactured predominantly from cellulose and to a lesser degree from recycled paper or with mixed-in wood. Such tissues have recently attained significant importance, so that this term is now used internationally as a collective name for sanitary papers. These are employed in the production of toilet paper and numerous other sanitary products, such as facial tissues, paper napkins and paper towels.

Paper towels represent only about 6% of the total quantity of paper produced in Germany, but they greatly affect the quality of life of the population, so that products made from these types of paper are very much in demand. Most important are the so-called tissue papers, which are characterized by a very loose and voluminous layer structure. They are creped and embossed to increase the volume and optimize specific technical properties. Tissue papers are assembled in single-ply or multiple-ply form into facial tissues, toilet paper or paper towels. The corresponding products must meet a number of specific requirements. For example, they must be able to withstand plenty of moisture, have a minimum mechanical strength, and must be physiologically harmless and also soft.

The softness of tissue paper is a subjectively perceived property, which is determined and evaluated in the industrial practice with sensors according to defined, but not uniformly standardized methods.

Softness is an exclusively subjective property which cannot be unambiguously described in scientific or technical terms, because the subjective perception of softness is a result of a combination of many product features. This complex combination will be described in more detail below.

Softness is foremost a tactile property, i.e., a property perceived by touching. The following situations have to be distinguished:

Perception of softness by touching the surface
In this process, the finger tips move across the product which is laid out flat. Impacting the perception is the surface structure of the product and the property of the dam produced by the fingertip. The latter is determined to a large degree by the pore volume and the viscoelasticity of the product. Free fiber ends protruding from the surface also influence the surface softness.

Perception of softness by folding and/or crumpling
In use, tissue products are folded and/or crumpled, whereby the softness perception is here dominated less by the surface properties than by the volume properties. The pore volume of the sheet has as much of an effect as the viscoelasticity.

The softness of the tissue product is not only evaluated by the sense of touch. The other sensory organs are also important. For example, if crackling sounds are produced when the softness of tissue is evaluated by touch, then the perceived softness will subconsciously be diminished. Likewise, the results of the evaluation can also be impacted by a distinct and objectionable smell.

The methods known to date for measuring and evaluating softness will now be briefly described.

According to the present state-of-the-art, the softness of tissue and tissue products is evaluated by touch by engaging a "panel"—a group with a defined number of people—of qualified test persons, in a so-called "panel test." A touch test is used by all manufacturers and processors. Part of the tests are always the aforementioned tactile evaluation of this surface characteristics and an evaluation of the folding and crumpling properties. Procedures and evaluation criteria are different. Softness evaluations can therefore not transferable from one manufacturer to another and are very time consuming and also expensive because of the large number of persons involved.

Moreover, a so-called "Kawabata" evaluation system (C. M. Carr and J. C. Roberts, "Technology transfer-a quality control toll from textile industry". Paper Technology, No. 11, 1993, P. 27-28) has been developed for textile materials. The system measures a large number of parameters and derives an assessment in a complex manner which will at this point not be described in detail. The tensile strength, shear strength, flexural strength, compressibility, thickness and mass per unit area as well as the surface structure are measured. This test is very complex and only rarely leads to a reproducible assessment of the softness.

A method proposed by H. Hollmark ["Evaluation of tissue paper softness", Tappi Journal, 1983, No. 2, p. 97-99] and referred to as "Surface Softness Analyzer" for evaluating the surface of softness operates on the basis of a record player. A sample of the tissue paper is placed on the turntable, which rotates for a total time of about 15 seconds. During this time, the amplitude and frequency of the surface roughness are measured with a modified "pickup." A performance parameter for the surface softness is derived from both measurement values.

Similar approaches are described in the documents U.S. Pat. No. 3,026,726 and DE 30 20 348 A1, which also use a turntable for measuring the surface quality of paper.

Also known is a system referred to as "Handle-O-Meter." With the Handle-O-Meter, a tissue sample is placed over a groove having a defined width. A blade presses the sample into the groove, and the required force is measured. This concept is also employed in the U.S. Pat. No. 3,151,483.

Another experimental method is described in the literature with the title "WABY-Faktor" [R. S. Ampulsiki, W. U. Spendel, A. H. Sawdai und B. Weistein, "Methods for measurement of the mechanical properties of tissue paper", International Paper Physics Conference, Tappi Proceedings, 1991, p. 19-22]. This method refers to the ratio of sample flexibility to tear force. The flexibility in turn is defined by the ratio of tensile force (20 N/m) to resulting elongation. In the published literature, the flexibility is viewed as having a specific relation to the softness.

Also defined in [R. S. Ampulsiki, W. U. Spendel, A. H. Sawdai und B. Weistein, "Methods for measurement of the mechanical properties of tissue paper", International Paper Physics Conference, Tappi Proceedings, 1991, p. 19-22] is the so-called physiological surface softness which is defined as a factor that is measured when a tissue sample is scanned with a profilometer in the machine direction. The obtained signal is Fourier-transformed, producing an amplitude-frequency representation, which requires suitable filtering before being adapted to the subjective tactile sensation. The integral yields the so-called PSS factor which is supposed to correlate with the softness perception.

Finally, the softness can be experimentally evaluated with the method of the "Circular Pendulum according to Bekk".

This is a circular pendulum, which is placed on the sample to be examined and rotated out of the rest position until the limit stop touches the sample surface. When the pendulum is released, it oscillates about the rest position with a decreasing oscillation amplitude. The time until the oscillation has completely decayed is measured.

The known methods turn out to be very complex and expensive. Although the "panel test" produces results related to the softness, these results are only partially objective and do produce comparative measurement result which are manufacturer-independent. All other methods, in particular the "Kawabata" evaluation system and the "Circular Pendulum according to Bekk" have insufficient correlation with the subjective perception by the consumer or do not adequately differentiate and have therefore not gained acceptance in practical applications.

The complex process for determining the softness factors and/or the required time before a result is available, make it desirable to have a fast measurement and evaluation method which correlates with the subjective softness for routine practical use. In particular, the softness between different manufacturers of sanitary papers and/or textiles should be standardized to make a meaningful comparison possible.

It is therefore an object of the invention to provide a device and a corresponding method for quickly and reproducibly measuring the softness of sanitary paper and/or textiles.

In a first embodiment, the object is attained in conjunction with the features of the preamble of claim 1 by a device which includes an element disposed vertically on an axis, wherein the element is arranged for rotation relative to a stationarily positioned, at least single-ply, horizontally oriented sample of the sanitary paper or textile and configured for displacement along the axis relative to the sample when subjected to a defined penetration force applied orthogonally on the sample, wherein a vibration sensor is disposed in the region where the vibrations are generated between the sample and the element, with the vibration sensor recording the sound generated when the element operating on the sample rotates about the axis.

In a second modified embodiment, the object is further attained in conjunction with the features of the preamble of claim 2 by a device which includes an element disposed vertically on an axis, wherein the element is stationary relative to a rotatable, at least single-ply, horizontally oriented sample of the sanitary paper or textile, wherein the sample is configured for displacement along the axis when subjected to a defined penetration force applied by the element orthogonally on the sample, wherein a vibration sensor is disposed in the region where the vibrations are generated between the sample and the element, with the vibration sensor recording the sound generated when the sample operating on the element rotates about the axis.

With the devices of both embodiments, a method according to the invention in conjunction with the features of the preamble of claim 19 can be performed, wherein a sound is generated, received and recorded in a specified measurement time interval by an element which is vertically positioned on an axis and rotatable relative to a stationary, at least single-ply horizontally oriented sample of the sanitary paper or textile and which operates in an orthogonal direction on the sample with a specified penetration force, or by an at least single-ply horizontally oriented sample of the sanitary paper or textile, which can rotate relative to a stationary element positioned vertically on an axis and which operates in an orthogonal direction on the stationary element with a specified penetration force, wherein the generated vibrations are evaluated in a vibration analysis by determining a sound spectrum or a frequency band, and wherein a specific softness of the sample is associated with each determined sound spectrum or frequency band.

In an advantageous embodiment of the invention, the two different embodiments are characterized in that the vibration sensor is arranged on the element or in the region of a holding device of the sample.

The sample is arranged on the holding device by forming a substantially flat sample plane, wherein the holding device can be implemented as a measurement housing, on which the sample can be attached with at least one holding element.

In an advantageous embodiment of the invention, the measurement housing has at least one opening on which the sample is attached, wherein the measurement housing may optionally be constructed to be partially open or closed, so that either an open sound region or a limited sound space can be formed for a sound field that is established between the element and the sample, with the vibration sensor disposed in this sound region.

The vibration sensor may be arranged outside or in the region of the holding device, or outside or in the region of the measurement housing.

In another advantageous embodiment of the invention, a force measuring device is provided, which is arranged in the region of the holding device of the sample depending on the force direction of the penetration force.

In yet another embodiment of the invention, the force measuring device can also be arranged on the element itself or in the region of the element for adjusting and measuring the penetration force of the element.

The force measuring device should be arranged so that depending if it is used in conjunction with the first embodiment where the movable element is moved relative to the stationary sample or with the second embodiment, where the movable sample is moved relative to the stationary element, the penetration force into the sample can be precisely determined.

The displacement is a measure for the elasticity of the sample and can be defined and evaluated depending on the material. To produce the same displacement, a different penetration force is required depending on the material so as to deform the sample to the desired degree.

It should also be noted that for both embodiments the penetration force of the element operates at any desirable angle relative to the sample, preferably orthogonally to a substantially horizontal sample plane.

The actual relative movement between the element and the sample for generating the sound with a force that was previously applied or is simultaneously applied to the sample, can be produced in different ways. In a preferred embodiment of the invention, the movable element or the movable sample is arranged, depending on the particular embodiment, so as to produce the sound by a rotation, translation or a pendulum oscillation, relative to the respective stationery component of the device.

For realizing the relative movement between the element and the probe and also for realizing the displacement and for adjusting the penetration force, the respective movable part of the device, the element or the sample is connected at, on one hand, with a mechanical or electrical or pneumatic or hydraulic drive, which can be directly or indirectly connected via a transmission means with the element or the sample.

In another advantageous embodiment of the invention, the vibration sensor is a microphone which is connected to a processing or calibration unit, wherein the microphone and/ or the processing and calibration unit is arranged in the region of the holding device or inside or outside the measurement housing.

According to one feature of the device, a temperature sensor and/or a humidity sensor for determining the temperature and/or the relative humidity is arranged in the measurement region, in the region of the holding device or in the measurement housing or in a climate chamber surrounding the device.

The design of the element, preferably the scraper element, can have different shapes. According to the invention, flat or concave or convex or acute contact surfaces with the sample can be implemented.

The element can be a flat plate in form of a separate component. The plate can also formed with contour-shaping elements oriented toward the sample, so that the different flat, concave, convex or acute shapes relative to the sample plane with the resulting contact surfaces can be formed.

A defined surface roughness can also be specified for the surface of the element oriented toward the sample.

The surface roughness can also be attained by arranging on the surface of the element oriented toward the sample identical or different sanitary paper or textile patterns, depending on the material of the sample, which can also be used to specify a defined surface roughness.

Lastly, the element, preferably the scraper element, is made of different materials having a suitable minimum hardness, wherein preferably plastics or metals with a predefinable surface roughness can be employed.

According to another characteristic property of both embodiments of the invention, the sample is arranged on the opening of the holding device or the measurement housing by forming a substantially flat sample plane, so that the sample is supported by a foil or plate, which is closed or is partially provided with openings, and which has different material thicknesses and/or material properties.

The method which can be implemented with both devices is characterized in that the vibration analysis is performed over the sound spectrum or the frequency band by evaluating the sound intensity and/or the sound level of the sound pressure in specified regions of the sound spectrum and/or the frequency band, wherefrom a complex performance parameter is computed which correlates with the softness of the sample.

In an advantageous embodiment of the invention, a calibration is performed before the measurement for determining the softness, a specific softness is associated with at least one reference sound spectrum or at least one reference frequency band in a specified region of the sound spectrum or the frequency band, wherein in another preferred embodiment, a complex performance parameter is also as associated therewith, which objectively combines different parameters of the sample softness.

In an advantageous embodiment of the invention, the received sound spectra or frequency bands are evaluated by performing a Fourier analysis which separates the individual vibrations of the generated sounds.

Overall, the method is essentially performed with the following steps. The sample is clamped and secured in the device of the invention (first or second embodiment) essentially flat. The force is then applied while the displacement is simultaneously measured, and the relative movement between the sample and the element is measured simultaneously or sequentially, whereby the sound is received and recorded with a vibration sensor in the specified measurement time interval, and the sound is then evaluated based on the sound spectrum or the frequency band and the performance parameter is computed. According to the invention, the performance parameter correlates with the softness.

To enable a comparison between the results, the softness is to be determined preferably under standard conditions at a temperature (T=23° C.) and a relative humidity ($\omega$=50%).

The preferred experimentally determined penetration force is in a range of about 0.01 N to about 1.5 N for tissue paper, wherein a penetration force of 0.1 N is preferred for single-ply samples.

For tear-resistant sanitary paper and textiles, forces greater than the indicated range of 1.5 N can be defined.

The device of the first and second embodiment and the associated method, which can be rapidly performed, advantageously enable a manufacturer-independent objective assessment of the softness based on the evaluation of a performance parameter.

An exemplary embodiment of the invention will now be described in detail with reference to FIG. 1—first embodiment.

FIGS. 2 and 3A to 3C show additional features of the first embodiment of FIG. 1, but can also be applied to both embodiments.

In the description of the first embodiment, the difference between the first and the second embodiment is partially described; however, the second embodiment is not separately illustrated.

FIG. 1 shows the device 100 according to the invention for determining the softness of sanitary papers.

FIG. 2 shows a top view of an element, in particular a scraper element 106, which can be used equally in both embodiments.

FIGS. 3A to 3C show different forms of the scraper element 106, which can also be used in both embodiments.

As shown in FIG. 1, the device 100 includes a movable element 106, which will be referred to hereinafter as scraper element. The scraper element 106 is connected with a drive 102 via a transmission means 104—in the exemplary embodiment a drive shaft—, wherein a first motor 134, which is schematically illustrated in the drive 102, causes the scraper element 106 to perform a rotation about an axis 124. The drive 102 includes a second motor 136 which is shown next to the drive 102, so that the scraper element 106 is capable of performing a movement along the axis 124 in addition to the rotation about the axis 124. This movement $\Delta s$ can be defined and measured by way of a distance measuring device 132, wherefrom a parameter can be derived which corresponds to the elasticity of a sample P of the sanitary paper or textile and which can be used to compute the softness.

In the present exemplary embodiment, the scraper element 106 is arranged for rotation relative to the sample P and can also move—in this case the height can be adjusted—relative to the sample P. The adjustment is hereby vertical in relation to the sample P which is positioned horizontally.

The invention is not limited to a rotation relative to the sample P, and the invention also includes translatory movements or pendulum oscillations which the scraper element 106 can perform relative to the sample P, wherein the translatory movements or pendulum oscillations relative to the movements of the sample P are coupled with an adjustment motion by which a penetration force F onto the sample P can be specified. The penetration force F exerted onto the sample P and its exemplary effective direction is shown in FIG. 1 by arrows pointing in the direction of the sample P. Of course, an effective direction of the penetration force F that operates not vertical in relation to the horizontal sample P, but at an angle that is different from 90°, is also feasible.

In the exemplary embodiment, a measurement housing 108, which is constructed of vertical sidewalls and a horizontal bottom wall, is associated with the scraper element 106. The measurement housing 108 is not absolutely necessary for performing the method. Basically, the device 100 must only have a holding device to which the sample P can be attached.

In the exemplary embodiment, the sample P is attached by way of the side walls of the measurement housing 108, on which the sample P of the respective test material [sanitary paper or textile] is placed or mounted, for example by simply folding the marginal regions of the sample P. The sample can preferably be attached by a sealing element 112, in particular a rubber lip, and secured with a holding element 114, preferably a clamp, a rubber band, and the like. This arrangement results in a sample plane 122 which is arranged above a measurement space 110 in the measurement housing 108.

A measurement space 110 is also not absolutely necessary for the invention. The sample plane 122 could also be formed above an open area without corresponding sidewalls or bottom walls of the measurement housing 108 and without the forming an enclosed measurement space 110.

Preferably, such measurement housing 108 with a measurement space 110 is provided, in which a temperature sensor 128 or a humidity sensor 130 is arranged for measuring a temperature T and/or a relative humidity $\omega$, respectively. The arrangement is preferably implemented on one of the sidewalls of the measurement housing 108, wherein an arrangement can, of course, also be implemented independent of a measurement housing 108 if the corresponding sidewalls are omitted.

It should be mentioned that device 100 can also be arranged in an air-conditioned room or a climate chamber having a constant temperature and/or a constant relative humidity, wherein the measurement is preferably standardized by employing standard conditions, namely a temperature T=23° C. and a relative humidity of $\omega$=50%, as is known in the art.

According to the invention, a vibration sensor 116 is arranged inside the measurement housing 108 or in the region of a holding device and connected with an evaluation and calibration unit 126.

In the exemplary embodiment, the evaluation and calibration unit 126 is arranged in the vibration sensor 160. These components 116, 126 can also be implemented separately, so that the illustrated arrangement is meant to serve only as an example.

FIG. 1 shows that the measurement housing 108 is arranged on force measuring devices 118 which are stationary relative to the base 120 and which can be used to measure a penetration force F which operates indirectly on the sample P.

The vibration sensor 116 can basically be any type of measuring device capable of receiving and recording sound spectra and frequency bands, because the method of the invention performs a vibration analysis of the sounds generated between the scraper element 106 and the sample P.

FIG. 2 shows a top view A-A of a possible basic structure of the scraper element 106, which is formed of a circular scraper housing 106A having scraper housing reinforcements 106B and 106C. Other noncircular shapes also feasible.

FIGS. 3A to 3B shows a scraper element 116 in cross-sectional views through the scraper element 106, indicating that different scraper shapes 106 can be implemented. FIG. 3A shows a scraper which is essentially configured as in FIG. 1, but is implemented with reduced corner regions, wherein the scraper element 106 in FIG. 3A forms an essentially flat contact surface with respect to the sample P. Elimination of edges/corners can reduce potential damage to the sample P during the measurement time $\Delta t$. The contact surface of the scraper element 106 according to FIG. 3B is defined by a conical acute scraper element 106. In another possible embodiment depicted in FIG. 3C, the scraper shape 106D is convex, which also results in a corresponding characteristic contact surface with the sample P. Not illustrated, but also feasible is, for example, a concave shape of the scraper element 106.

The scraper element 116 can also be formed as a separate component in form of a flat plate (not illustrated), which also provides a flat contact surface.

Before describing the method of the invention, it should be mentioned that the device with a similar functionality can be implemented so that the at least single-ply sample P is movable, whereas the scraper element 106 is configured as a stationary part.

The drive 102 is then accordingly arranged on the holding device or on the formed measurement housing 108, so that the sample P can move across the holding device, depending on the contemplated type of motion, either by a rotation, translation, or in form of a pendulum oscillation with respect to the scraper element 106. In addition, the holding device or the measurement housing 108 of the sample P must then move in the direction of the scraper element 106 in order to define the penetration force F and/or the displacement $\Delta s$. The force measuring device 118 is then located, like in the first exemplary embodiment, on the stationary scraper element 116, so that the specified penetration force F of the movable sample P can be adjusted and measured. The distance measuring device 132 is likewise arranged on the movable part, namely the sample P or the holding device of the sample.

The method of the invention will now be described in more detail with reference to FIG. 1, with the basic principles of the methods similarly applying to the device of the unillustrated second embodiment, where the sample P is movable and the scraper element 106 is stationary.

The method for determining the softness of sanitary papers is performed as follows: a suitable sample P is removed from an existing supply of sanitary paper or a textile and clamped via the holding element 114 onto the measurement housing 108. The height-adjustable scraper element 106 is first moved by the second motor with a specified penetration force onto the slightly flexible sample P. An adjustable force of 0.1 N is preferably applied, wherein an adjustment displacement $\Delta s$ is also defined and subsequently measured and monitored.

The scraper element 106 is set in rotation by the drive 102 and produces during a specified time interval $\Delta t$ a sound, which propagates in wave form by generating complex vibrations in the region of the sample P. A preferred rotation speed is about 1 Hz, wherein it will be understood that higher and lower speeds can be used, which are always selected by taking into consideration that the sample (P) should not tear.

The method can also be implemented so that the displacement $\Delta s$ and the rotation commence simultaneously, producing a sound while the scraper element penetrates into the sample P during its rotation.

These vibrations, which are within or outside the human auditory range, form the basis for a vibration analysis and for determining a sound spectrum or frequency band, wherein the term sound is also used for vibrations within or outside the human auditory range.

The vibrations are recorded by the sound sensor 116 which is according to FIG. 1 arranged in the measurement space 110 in which a corresponding sound field is formed.

It should be noted that the sound can, of course, also be recorded outside the measurement space 110, for example according to FIG. 1 also above the sample P.

A measurement space 110 with defined conditions, such as the relative humidity ω=50% and the temperature T=23° C. and constant environmental conditions (without extraneous noise, etc.) can be used for comparing measurements.

The received and recorded vibrations are evaluated in a vibration analysis performed by the evaluation and recalibration unit 126 by integrating a computer or a data processing device or the like into the system of the invention, wherein preferably a sound intensity I and/or a sound level $L_p$ of the sound pressure p is measured in specified regions of the sound spectrum and/or frequencies of the frequency band. A characteristic parameter K which correlates with the softness of the sample can be determined from these values by Fourier analysis.

To characterize the softness, a specific softness and a characteristic parameter K related to the softness is associated with a reference sound spectrum or a reference frequency band.

With these reference sound spectrum and reference frequency bands, respectively, the measured and subsequently computed data can be associated with a characteristic parameter K correlating with the softness.

A computer and the like used for this evaluation can, of course, also used for the controlling the movement of the scraper element 106 with respect to the stationary sample P, or vice versa (depending on the selected embodiment).

The computer can, of course, also control and regulate the rotation/translation/pendulum motion of the scraper element 106 and the displacement Δs of the sample P, or vice versa, as well as the specified time interval Δt. The penetration force F can also be controlled or regulated by the computer.

Experiments have shown that the subjective perception of softness can be objectively measured with the aforedescribed measurement method and with the illustrated device 100 by determining a number of parameters, for example smoothness, roughness, surface softness, compressibility and the sound observed when a sample P is crumpled, because the measurement results correlate well with the subjective manually obtained results in tests performed by test persons.

The method can therefore be used for determining an objective softness independent of the manufacturer and therefore offers the possibility for standardization.

LIST OF REFERENCE SYMBOLS

100 device
102 drive
104 transmission means (drive shaft)
106 element (scraper element)
106A scraper housing
106B scraper housing reinforcement
106C scraper housing reinforcement
106D scraper shape
108 measurement housing
110 measurement space (sound field)
112 sealing element (rubber lip)
114 holding element
116 vibration sensor
118 force measuring device
120 base
122 sample plane
124 axis
126 evaluation and calibration unit
128 temperature sensor (T) [temperature]
130 humidity sensor (ω) [relative humidity]
132 distance measuring device
134 first motor
136 second motor
F penetration force
P sample
p sound pressure
f frequency
I sound intensity
L sound pressure level
K characteristic parameter for softness
Δt measurement time interval
Δs distance difference

The invention claimed is:

1. A device for determining softness of an at least single-ply sanitary paper or textile, wherein the device comprises a scraper element disposed vertically on an axis, wherein the scraper element is:
   (i) arranged for rotation relative to a stationarily positioned, at least single-ply, horizontally oriented sample of the sanitary paper or textile and configured for displacement along the axis relative to the sample, which is secured on a measurement housing, when subjected to a defined penetration force applied orthogonally on the sample, or
   (ii) stationary relative to a rotatable, at least single-ply, horizontally oriented sample of the sanitary paper or textile, with the sample, which is secured on a measurement housing, being configured for displacement along the axis when subjected to a defined penetration force by the scraper element applied orthogonally on the sample
   such that the scraper element penetrates into the sample while deforming the sample, wherein a vibration sensor is disposed in the region where vibrations are generated between the sample and the scraper element, with the vibration sensor configured to record sound generated from the vibrations when the scraper element, operating on the sample, rotates about the axis or when the sample, operating on the scraper element, rotates about the axis.

2. The device according to claim 1, wherein the vibration sensor is arranged in the sound field of the sound independently or on the device or on the scraping element itself or in a region of a holding device of the sample.

3. The device according to claim 2, wherein the sample is arranged on the holding device by forming a substantially flat sample plane, wherein the holding device comprises essentially the measurement housing, on which the sample is attachable with at least one holding element.

4. The device according to claim 3, wherein the scraper element has, as a component part, a flat plate or is formed as a single piece or as several pieces with contour-forming elements oriented towards the sample, so that several shapes are formable relative to the sample plane, which form flat or concave or convex or acute contact surfaces with the sample.

5. The device according to claim 4, wherein a defined surface roughness can be specified for a surface of the scraper element oriented toward the sample.

6. The device according to claim 4, wherein identical or different sanitary paper or textile patterns for the sample are arranged on a surface of the scraper element oriented toward the sample.

7. The device according to claim 3, wherein the sample is supported by a foil or plate, which is closed or is partially provided with openings, and which has different material thicknesses and/or material properties.

8. The device according to claim 1, wherein the measurement housing comprises at least one opening on which the sample is attached, wherein the measurement housing is optionally constructed to be partially open or closed, so that either an open sound region or a limited sound space is formed for a sound field forming between the scraper element and the sample, with the vibration sensor disposed in this sound region.

9. The device according to claim 1, wherein the vibration sensor is arranged outside or in a region of a holding device, or outside or in a region of the measurement housing.

10. The device according to claim 1, wherein a force measuring device is provided for adjusting and measuring the penetration force of the scraper element, wherein depending on the force direction of the penetration force, the force measuring device is arranged in a region of a holding device of the sample.

11. The device according to claim 1, wherein a force measuring device is provided for adjusting and measuring the penetration force of the scraper element, wherein depending on the force direction of the penetration force the measuring device is arranged on the scraper element itself or in a region of the scraper element.

12. The device according to claim 1, wherein a distance measuring device is provided for measuring the penetration depth of the scraper element, with the distance measuring device configured to define an adjustment range of the scraper element or of the sample and/or measuring the adjustment range as a function of a material of the sample and the penetration force as a parameter for the elasticity of the sample.

13. The device according to claim 1, wherein the penetration force of the scraper element operates at any angle relative to the sample.

14. The device according to claim 1, wherein the scraper element or the sample is arranged so as to be movable by a rotation, translation or pendulum oscillation, thereby producing the sound.

15. The device according to claim 1, wherein the relative movement of the scraper element or the sample, on one hand, and the adjusting motion of the element or the sample for adjusting the penetration force, on the other hand, is accomplished with a mechanical or an electrical or a pneumatic or a hydraulic drive, which is directly or indirectly coupled with the scraper element or with the sample via a transmission means.

16. The device according to claim 1, wherein the vibration sensor is a microphone which is connected to a processing or calibration unit, wherein the microphone and/or the processing and calibration unit is arranged in the region of the holding device or inside or outside the measurement housing.

17. The device according to claim 1, wherein a temperature sensor and/or a humidity sensor for determining the temperature and/or the relative humidity is arranged in the measurement region, in the region of the holding device or in the measurement housing or in a climate chamber surrounding the device.

18. The device according to claim 1, wherein the scraper element is comprised of different materials having a suitable minimum hardness.

19. A method for determining softness of an at least single-ply sanitary paper or textile, wherein a sound is generated, received and recorded in a specified measurement time interval by a scraper element which is vertically positioned on an axis and rotatable relative to a stationary, at least single-ply horizontally oriented sample of the sanitary paper or textile and which operates in an orthogonal direction on the sample with a specified penetration force, or by an at least single-ply horizontally oriented sample of the sanitary paper or textile, which can rotate relative to a stationary scraper element positioned vertically on an axis and which operates in an orthogonal direction on the stationary scraper element with a specified penetration force, wherein the sample of the sanitary paper or textile is secured to a measurement housing, wherein the scraper element is configured to penetrate into the sample while deforming the sample, wherein vibrations of the generated sound are evaluated in a vibration analysis by determining a sound spectrum or a frequency band, and wherein a specific softness of the sample is associated with each determined sound spectrum or frequency band.

20. The method according to claim 19, wherein the vibration analysis is performed over the sound spectrum or the frequency band by evaluating the sound intensity and/or the sound level and/or the frequencies of the sound pressure in specified regions of the sound spectrum and/or the frequency band, wherefrom a complex performance parameter is computed which correlates with the softness of the sample.

21. The method according to claim 19, wherein before the measurement for determining the softness a calibration is performed, in a specified region of the sound spectrum or the frequency band, a specific softness is associated with at least one reference sound spectrum or at least one reference frequency band or a complex performance parameter computed therefrom.

22. The method according to claim 19, wherein the received sound spectra or frequency bands are evaluated with a Fourier analysis which separates the individual vibrations of the generated sounds.

23. The method according to claim 19, wherein
the sample is secured in a device essentially flat,
the application of the force and the relative movement between the sample and the scraper element is performed and measured simultaneously or sequentially,
the sound is received and recorded in the specified measurement time interval, and
the sound is lastly evaluated and computed from the sound spectrum or the frequency band by determining the performance parameter.

24. The method according to claim 19, wherein comparing the results, the softness is determined preferably under standard conditions at a temperature of about 23° C. and a relative humidity of about 50%.

25. The method according to claim 19, wherein the specified penetration force is in a range of about 0.01 N to about 150 N for sanitary paper, and in the same range or above for textiles.

* * * * *